United States Patent [19]
Cooper

[11] Patent Number: 5,683,417
[45] Date of Patent: Nov. 4, 1997

[54] SUTURE AND METHOD FOR ENDOSCOPIC SURGERY

[76] Inventor: William L Cooper, 2448 E. 81st, Suite 1600, Tulsa, Okla. 74137

[21] Appl. No.: 696,684

[22] Filed: Aug. 14, 1996

[51] Int. Cl.⁶ .................................................. A61B 17/04
[52] U.S. Cl. ........................................ 606/223; 606/230
[58] Field of Search ..................... 606/221, 224, 606/228, 232, 230

[56] References Cited

U.S. PATENT DOCUMENTS

| | | | |
|---|---|---|---|
| 3,123,077 | 3/1964 | Alcamo | 128/335.5 |
| 3,559,652 | 2/1971 | Banitt | 128/334 |
| 3,570,497 | 3/1971 | Lemole | 128/335.5 |
| 3,845,772 | 11/1974 | Smith | 128/335 |
| 4,548,202 | 10/1985 | Duncan | 128/334 |
| 5,053,047 | 10/1991 | Yoon | 606/223 |
| 5,207,694 | 5/1993 | Broom'e | 606/148 |
| 5,312,436 | 5/1994 | Coffey et al. | 606/228 |
| 5,330,503 | 7/1994 | Yoon | 606/223 |
| 5,350,798 | 9/1994 | Linden et al. | 525/41 |
| 5,372,146 | 12/1994 | Branch | 128/898 |
| 5,391,173 | 2/1995 | Wilk | 606/144 |
| 5,403,346 | 4/1995 | Loeser | 606/228 |
| 5,413,585 | 5/1995 | Pagedas | 606/232 |
| 5,425,747 | 6/1995 | Brotz | 606/228 |
| 5,437,680 | 8/1995 | Yoon | 606/139 |
| 5,486,547 | 1/1996 | Matsuda et al. | 523/111 |
| 5,496,872 | 3/1996 | Constancis et al. | 523/118 |
| 5,500,000 | 3/1996 | Feagin et al. | 606/232 |
| 5,522,896 | 6/1996 | Prescott | 623/16 |

*Primary Examiner*—Gary Jackson
*Attorney, Agent, or Firm*—Head Johnson & Kachigian

[57] ABSTRACT

A suture for particular use in endoscopic surgery includes a distal end needle, a preferably braided suture body, and a bulbous proximal end. The method includes stitching the tissue, then passing the needle/distal end through the bulbous proximal end, where the body of the suture is held frictionally or adhesively under proper tension.

12 Claims, 2 Drawing Sheets

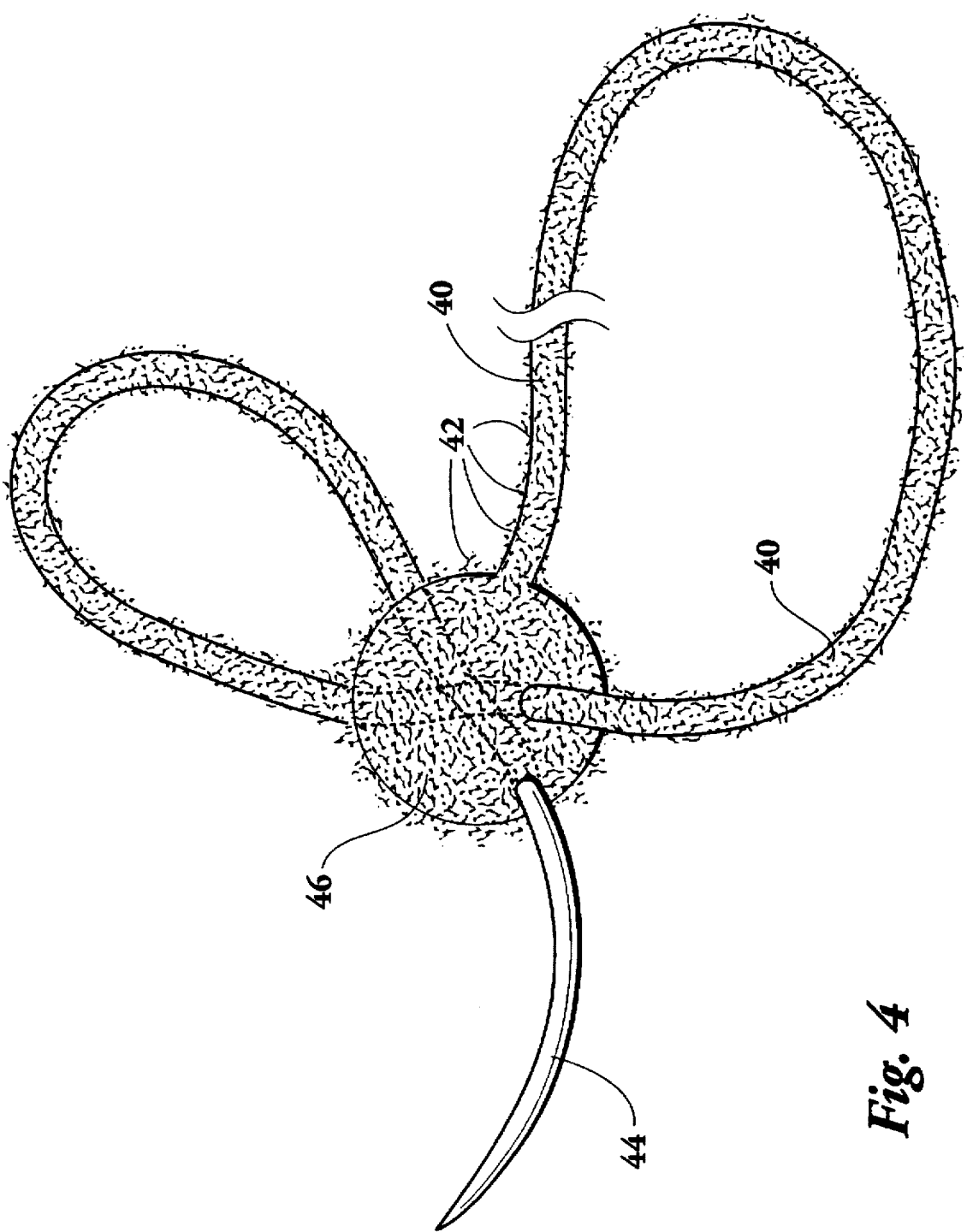

SUTURE AND METHOD FOR ENDOSCOPIC SURGERY

BACKGROUND OF THE INVENTION

1. Field of the Invention

The present invention relates to a suture for particular use in endoscopic surgery and methods for suturing using such suture devices.

Sutures for closing incisions or wounds are well known in the prior art. Such sutures or ligatures are often to attached to the shank end of a needle or have a needle incorporated as a part of the suture at the distal end. As is well known sutures are utilized by physicians to make stitches for closing tissue, incisions or wounds so that they may heal. Sutures are available in a wide variety of materials including monofilament, braided material, cat gut, silk, nylon, polyester, polyolefins such as polypropylene, linen, cotton as well as bioabsorbable materials, such as polyglactin.

Endoscopic surgery also known as laproscopic surgery is a popular and a preferred method over open tissue surgery due to greatly reduced trauma with faster wound healing time for the patient. A typical form of endoscopic surgery, or minimally invasive surgery, is that in which a small puncture is made in the body by an instrument called a trocar. Medical instruments are then inserted through a cannula, which is a sleeve that surrounds the trocar and provides a port of entry after the trocar is withdrawn. A miniaturized video camera is inserted through the cannula, enabling the surgical team to see what is happening inside the patient's body. Types of common endoscopic surgical procedures include arthroscopy, laparoscopy, and gastroentroscopy. Such surgery has achieved cost savings to patients because of shorter hospital stays or surgery in non-hospital or out-patient surgery sites. Variety of sutures and methods have been proposed for special use in endoscopic procedures. See, for example, U.S. Pat. Nos. 5,437,680; 5,053,047; and 5,330,503. Such devices have attempted to improve on prior art sutures and methods for suturing tissue. Heretofore endoscopic surgery has used such devices as staples, clips, clamps or other fasteners that have not provided sufficient means to obtain adjustable tensions during the suturing process. That is, one of the difficulties in endoscopic surgery is the ability to obtain the proper tension to pull the tissue together and retain it. To tie knots in the suture material during the endoscopy, is much more difficult than in an open wound. Hence there is a great need for suture devices especially in endoscopic surgery that permit surgeons to secure and tie knots quickly and with controlled tension.

SUMMARY OF THE INVENTION

It is a primary object of the present invention to provide suture devices and method for quickly connecting tissue without traditional knotting, particularly during endoscopic surgery.

Another object of the invention is to provide a surgical suture which can place tension to draw the tissue being treated together without having to tie a knot or use a ligature of any sort in particular.

In particular, its primary object to provide suture devices wherein the suture includes, at its distal end, a needle formed as a part of this suture. The proximal end includes a bulbous or spherical member. The bulbous member at the proximal end is capable of being punctured with the sharp distal end of the suture, to be received through the bulbous member which includes means therein to retain the suture body under the required tension. In one embodiment, the body of the suture includes barbs or whiskers projecting therefrom or at an acute angle that is directed toward the proximal end so that the suture body becomes locked to the bulbous member.

In another embodiment the bulbous end includes a sealed pharmaceutically acceptable adhesive. Once penetrated by the needle and the suture body will quickly set once the suture has been positioned with the proper tension thereto. The chemical adhesive is capable of bonding with or to the suture after the suture has penetrated through the bulbous member. The adhesive or bonding material will allow enough time for the suture to be positioned yet capable of "setting up" quickly enough (within a few seconds) that the surgeon can resect the extra portion of suture and leave the closure intact.

Another object of the invention is to provide a method for suturing tissue especially during laproscopic or endoscopic procedures. The surgeon utilizing a suture having a sharp distal end and bulbous proximal end penetrates the tissue at a entry point with the sharpened distal end. The suture is then passed through the tissue to be brought together and ultimately extends out through an exit point until the bulbous proximal end substantially abuts the entry point. The sharpened distal end is then caused to puncture the bulbous proximal end and the suture body pulled under tension away from the entry point and retained to the bulbous end. A suture body with resilient barbs or whiskers are retained to the bulbous end and especially so if the barbs or whiskers suture are at an acute angle directed towards the proximal end. The opening formed within the bulbous end after puncturing will allow the suture to be pulled therethrough to the desired tension, but will resist its return.

A yet further object of the invention is to provide a bulbous member at the proximal end being soft enough to be penetrated by the sharp distal end but also is sufficiently rigid enough to provide frictional resistance to the suture body to allow proper tension and yet prevent the suture from slipping back through it and separating therefrom. The use of braided suture material is especially applicable in view of its frictional characteristics.

Other objects and advantages of the invention will become more apparent from the following description of the preferred embodiments taken in conjunction with the accompanying drawings.

BRIEF DESCRIPTION OF THE DRAWINGS

FIG. 4 is a partial sectional view of another form of the invention.

DETAILED DESCRIPTION OF THE PREFERRED EMBODIMENTS

Figure 1:
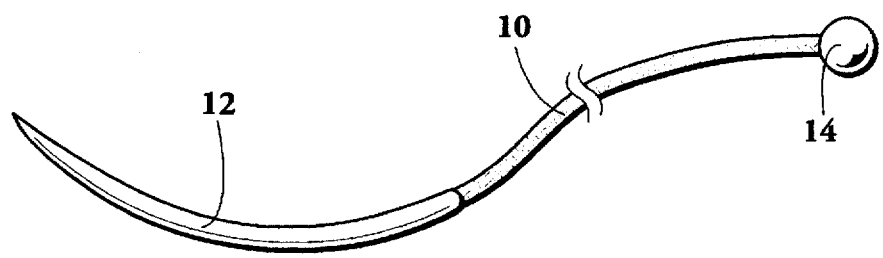
FIG. 1 is a elevational view of a typical suture according to this invention.

A typical suture device, in accordance with this invention, is illustrated in FIG. 1 and includes a flexible body portion 10, having a sharp distal or needle end 12 for penetrating, not only the tissue to be sutured, but also the enlarged bulbous end 14 at the proximal end of the suture. The suture can be made of bioabsorbable material, to remain in the tissue to be absorbed therein.

Figure 2A:
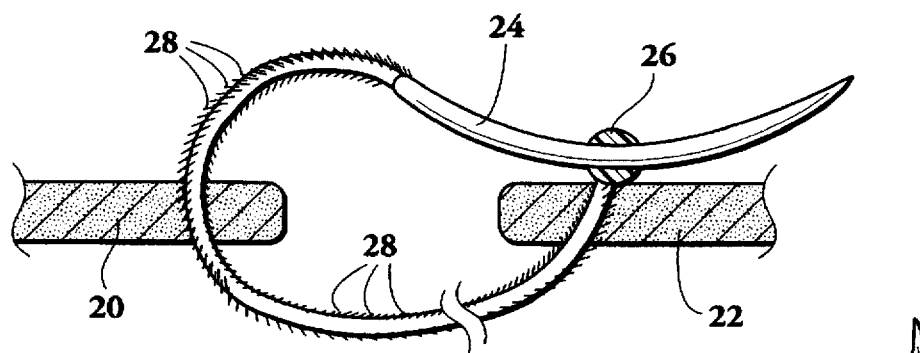
FIG. 2A is an elevational view, partly in cross section, a depicting the initial step of the suture closing system according to this invention.
Figure 2B:
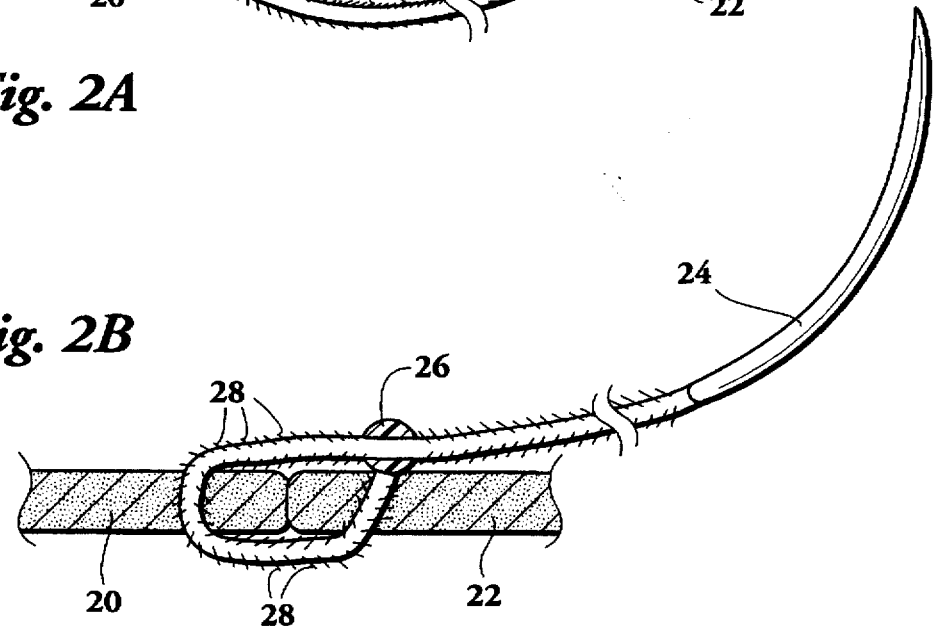
FIG. 2B is an elevational view depicting the final step in closing the wound or tissue.

In FIGS. 2A, 2B, a section of tissue 20 is to be joined with tissue 22. The suture in this instance includes a needle 24 at the distal end and a bulbous portion 26 at the proximal end, the suture itself is made up of bioabsorbable material having resilient barbs or whiskers 28 which project from the main body at an acute angle that is directed towards the proximal end. This form of suture thus allows the suture to pass essentially one way through the tissue 20 and 22 and thence, as shown in FIG. 2B, through the bulbous member 26 at the proximal end where said barbs will be retained and locked at the tension desired by the surgeon.

Figure 3:
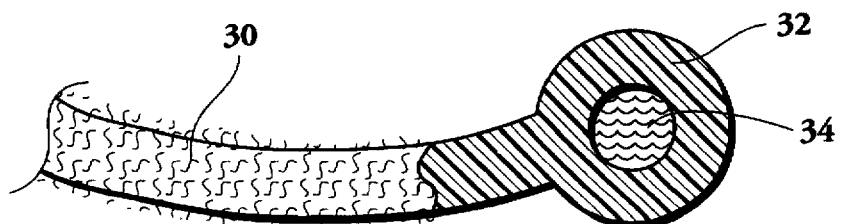
FIG. 3 depicts of further embodiment of the invention.

FIG. 3 is an alternate embodiment wherein at the proximal end of a braided suture 30 is a bulbous/spherical member 32 which contains, in the center thereof, a pharmceutically acceptable bonding or adhesive material 34. When the sharpened distal end penetrates the bulbous end it will communicate with and activate the bonding material 34 which will set up within a desired time period, e.g., a few seconds after the surgeon has placed and held the suture under the proper tension to hold the tissue together. Examples of adhesives are disclosed in U.S. Pat. Nos. 5,350,798; 5,457,141; 5,496,872; 5,350,798; and 3,559,652, which are incorporated herein by references.

FIG. 4 represents a further form of the invention wherein the suture 40 is so formed of a substantial random fluff or fuzzy texture of fine light particles or fibers 42. The suture 40 could be a loosely braided type. The suture includes a needle 44 as a distal end and a random matted bulbous proximal end 46, through which, the suture is passed at least once. The required tension to hold the tissue together is maintained by the interlocking of the random fibers 42 with the matted fibers of the bulbous end.

Whereas, the present invention has been described in relation to the drawings attached hereto, it should be understood that other and further modifications, apart from those shown or suggested herein, may be made within the spirit and scope of this invention. For instance, the suture and methods disclosed are applicable to open wound suturing.

What is claimed is:

1. A suture comprising a flexible elongate body member having a sharp distal end and a proximal end;

said proximal end having a bulbous member formed as a part thereof;

said bulbous member capable of being punctured with said sharp distal end, be received therethrough and with means to retain said body member therein.

2. The suture of claim 1 wherein said bulbous end includes a pharmaceutically acceptable adhesive.

3. The suture of claim 1 wherein said elongate body member includes resilient barbs projecting therefrom at an acute angle directed toward the said proximal end.

4. The suture of claim 1 wherein said suture is a bioabsorbable material.

5. The suture of claim 1 wherein said suture is one from the group of monofilament, polyolefins, polyester, silk, gut materials.

6. The suture of claim 1 wherein said suture is formed with random fuzzy fibers terminating in a random matted bulbous proximal end.

7. The suture of claim 6 wherein said suture is braided and body absorbable.

8. A method of suturing tissue in an anatomical cavity during laproscopic or endoscopic procedure comprising the steps of:

penetrating the tissue at an entry point with a sharpened distal end of an elongate suture material having a bulbous proximal end;

passing the suture through the tissue and ultimately out through an exit point in said tissue until said proximal end substantially abuts the said entry point;

inserting said sharpened end into and through said bulbous proximal end;

tensioning said suture by pulling away from said entry point whereby means cooperating with said bulbous end will secure said suture therein.

9. The method of claim 8 wherein said elongate body member includes resilient barbs projecting therefrom at an acute angle directed toward the said proximal end.

10. The method of claim 8 wherein said bulbous proximal end contains a pharmaceutically acceptable and body absorbable adhesive, and maintaining said suture in tension until said adhesive has set.

11. The method of claim 8 wherein said suture is formed with random fuzzy fibers terminating in a random matted bulbous proximal end.

12. The method of claim 11 wherein said suture is braided and body absorbable.

* * * * *